(12) United States Patent
Kim

(10) Patent No.: US 10,004,619 B2
(45) Date of Patent: Jun. 26, 2018

(54) POLYMERIC STENT AND METHODS OF MANUFACTURING THE SAME

(71) Applicant: Suntech Co., Ltd., Seoul (KR)

(72) Inventor: Hyungil Kim, Seoul (KR)

(73) Assignee: DOTTER INTELLECTUAL PTE, LTD., Singapore (SG)

( * ) Notice: Subject to any disclaimer, the term of this patent is extended or adjusted under 35 U.S.C. 154(b) by 0 days. days.

(21) Appl. No.: 15/435,844

(22) Filed: Feb. 17, 2017

(65) Prior Publication Data

US 2017/0156900 A1 Jun. 8, 2017

Related U.S. Application Data

(60) Division of application No. 14/626,481, filed on Feb. 19, 2015, which is a continuation-in-part of
(Continued)

(30) Foreign Application Priority Data

Sep. 20, 2012 (KR) .................. 10-2012-0104473
Feb. 26, 2014 (KR) .................. 10-2014-0022859

(51) Int. Cl.
*A61F 2/915* (2013.01)
*B29C 59/16* (2006.01)
(Continued)

(52) U.S. Cl.
CPC ............... *A61F 2/915* (2013.01); *A61F 2/91* (2013.01); *B23K 26/0624* (2015.10);
(Continued)

(58) Field of Classification Search
CPC . B29C 2035/0838; B29C 59/165; A61F 2/86; A61F 2/90; A61F 2/91; A61F 2/915; B23K 26/0624
See application file for complete search history.

(56) References Cited

U.S. PATENT DOCUMENTS

| 5,508,378 A | 4/1996 | Ohara et al. |
| 5,928,280 A | 7/1999 | Hansen et al. |

(Continued)

FOREIGN PATENT DOCUMENTS

| WO | 97/09945 | 3/1997 |
| WO | 2007/142736 A2 | 12/2007 |

OTHER PUBLICATIONS

Park, Seung-Bae, "Notice of Grounds of Rejection (Korean Office Action)," dated Jun. 27, 2014 for corresponding Korean Application No. 10-2014-0022859 filed Feb. 26, 2014, English translated pp. 1-9.

(Continued)

*Primary Examiner* — Howie Matthews
(74) *Attorney, Agent, or Firm* — MH2 Technology Law Group, LLP

(57) ABSTRACT

A method of manufacturing a polymeric stent by forming a pattern on a polymer tube with a laser, where the pattern formed on the polymer tube comprises a plurality of repeating units comprising a plurality of unit cells, each having a V-shaped configuration and polymeric stents formed by the methods. The pattern may be formed on the polymer tube (e.g., polylactic acid tube) using a second harmonic generator laser in which a wavelength ranging from 940 nm to 1552 nm is converted.

9 Claims, 7 Drawing Sheets

Related U.S. Application Data application No. 13/929,237, filed on Jun. 27, 2013, now abandoned.

(51) Int. Cl.

| | | |
|---|---|---|
| *B23K 26/0622* | (2014.01) | |
| *A61F 2/91* | (2013.01) | |
| *B29C 43/02* | (2006.01) | |
| *B23K 26/359* | (2014.01) | |
| *B29L 31/00* | (2006.01) | |
| *B29C 35/08* | (2006.01) | |

(52) U.S. Cl.
CPC .. *B29C 59/165* (2013.01); *A61F 2002/91575* (2013.01); *A61F 2210/0004* (2013.01); *A61F 2230/0054* (2013.01); *A61F 2230/0069* (2013.01); *A61F 2240/001* (2013.01); *A61F 2250/0098* (2013.01); *B23K 26/359* (2015.10); *B29C 43/027* (2013.01); *B29C 2035/0838* (2013.01); *B29C 2043/028* (2013.01); *B29L 2031/7532* (2013.01)

(56) References Cited

U.S. PATENT DOCUMENTS

| | | |
|---|---|---|
| 6,565,598 B1 | 5/2003 | Lootz |
| 8,002,817 B2 | 8/2011 | Limon |
| 9,510,961 B2 | 12/2016 | Kim |
| 2002/0065553 A1 | 5/2002 | Weber |
| 2002/0108937 A1 | 8/2002 | Shapovalov et al. |
| 2003/0151053 A1 | 8/2003 | Sun et al. |
| 2004/0215312 A1 | 10/2004 | Andreas |
| 2004/0220660 A1 | 11/2004 | Shanley et al. |
| 2007/0034615 A1 | 2/2007 | Kleine |
| 2007/0156230 A1 | 7/2007 | Dugan et al. |
| 2008/0275537 A1 | 11/2008 | Limon |
| 2008/0281403 A1 | 11/2008 | Kavteladze |
| 2009/0319031 A1 | 12/2009 | Wang et al. |
| 2010/0244334 A1 | 9/2010 | Contiliano et al. |
| 2010/0262223 A1 | 10/2010 | Kleiner |
| 2010/0274349 A1 | 10/2010 | Lord et al. |
| 2011/0307050 A1 | 12/2011 | Harrington et al. |
| 2015/0230946 A1 | 8/2015 | Al-Lamee et al. |

OTHER PUBLICATIONS

Presentation by Hector M. Garcia-Garcia et al., entitled "Bioabsorbable Stents," Thoraxcentre, Erasmus Medical Center, the Netherlands, Oct. 22, 2012, pp. 1-39.

European Search Report dated Feb. 6, 2014 from European Patent Application No. 13185218.8, pp. 1-6.

Extended European Search Report dated Aug. 9, 2015 from European Patent Application No. 15156735.1, pp. 1-5.

Final Office Action dated May 19, 2016 in U.S. Appl. No. 14/626,584, pp. 1-26.

Non-Final Office Action dated Feb. 1, 2016 for U.S. Appl. No. 14/626,584, pp. 1-12.

Non-Final Office Action dated Oct. 10, 2017 for U.S. Appl. No. 15/282,500, pp. 1-9.

Non-Final Office Action dated Sep. 8, 2017 for U.S. Appl. No. 15/338,890, pp. 1-10.

Final Office Action dated Oct. 5, 2017 for U.S. Appl. No. 14/626,481, pp. 1-9.

Non-Final Office Action dated May 19, 2017 for U.S. Appl. No. 14/626,481, pp. 1-7.

European Office Action dated Aug. 28, 2017 for European Application No. 15156735.1, pp. 1-4.

80um   120um

POLYMERIC STENT AND METHODS OF MANUFACTURING THE SAME

CROSS REFERENCE TO RELATED APPLICATIONS

This application is a divisional application of U.S. application Ser. No. 14/626,481 (pending), filed 19 Feb. 2015, which claims priority to, and the benefit of, Korean Patent Application No. 10-2014-0022859, filed in the Korean Intellectual Property Office on Feb. 26, 2014, the entire disclosure of which is hereby incorporated by reference. U.S. application Ser. No. 14/626,481, filed 19 Feb. 2015, is a continuation-in-part of U.S. application Ser. No. 13/929,237 (abandoned), filed 27 Jun. 2013, which claims priority to and the benefit of Korean Patent Application No. 10-2012-0104473 filed in the Korean Intellectual Property Office on Sep. 20, 2012, the entire disclosures of which are hereby incorporated by reference.

FIELD

The field of the invention relates to polymeric stents, and in particular methods of manufacturing such devices.

BACKGROUND

In general, stents are expandable medical prostheses, and are used within body vessels of humans for a variety of medical applications. Examples include intravascular stents for treating stenosis, and stents for maintaining openings in the urinary, biliary, tracheobronchial, esophageal, and renal tracts, and inferior vena cava.

Typically, prior to placement, a stent will be maintained in a compressed state and delivered by a device designed to position the compressed stent at a treatment site, and then allow the stent to expand once in position. Commonly, stents are delivered to the treatment site by passage through the lumen of body vessels.

For example, in percutaneous transluminal angioplasty, an implantable endoprosthesis, that is, a stent is introduced through a delivery device, and is passed through body vessel conduits to a treatment site. After the stent approaches the treatment site, the stent is typically mechanically expanded, usually with the aid of an inflatable balloon, thereby being expanded within the body vessel. The delivery device is then retreated and removed from the patient. The stent remains within the vessel at the treatment site as an implant.

SUMMARY

Various objects, features, aspects and advantages of the inventive subject matter will become more apparent from the following detailed description of preferred embodiments, along with the accompanying drawing figures in which like numerals represent like components.

The present disclosure provides polymeric stents and methods for their manufacture using a laser. Compared to prior art polymeric stents, the stents described herein have superior properties with respect to mechanical strength as compared to prior art designs.

Thus in some embodiments there is provided a method for manufacturing a polymeric stent, comprising: forming a pattern on a polymer tube with a laser; wherein the pattern formed on the polymer tube comprises a plurality of repeating units comprising a plurality of unit cells, wherein each unit cell has a V-shaped configuration and comprises a first hinge portion having a first end and a second end, wherein the first hinge portion is bent inwardly to the unit cell and a second hinge portion having a first end and a second end, wherein the second hinge portion is facing the first hinge portion and bent outwardly from the unit cell; and a linker portion extended outwardly from a bent portion of the second hinge portion; wherein the repeating units are disposed such that an end of a linker portion of one repeating unit is connected to a bent portion of a first hinge portion of an adjacent repeating unit, or the first end of a first hinge portion and the first end of a second hinge portion of one repeating unit are connected to an end of a first hinge portion and an end of a second hinge portion of the adjacent repeating unit, respectively; and wherein the thickness of the unit cell and the strut of the linker portion is 80 to 160 μm.

In some embodiments of the method the pattern is formed on the polymer tube using a second harmonic generator laser in which a wavelength ranging from about 940 nm to 1552 nm or less is converted. In other embodiments, the second harmonic generator laser is a laser in which a wavelength ranging from 1000 nm to 1100 nm is converted. In some embodiments, the polymer tube is made from polylactic acid. In some embodiments a pulse width of the second harmonic generator laser is 10 ps or less. In some embodiments a pulse width of the second harmonic generator laser is 1 ps or less.

In some embodiments of the method an output wavelength of the second harmonic generator laser ranges from 470 nm to 776 nm. In some embodiments an output wavelength of the second harmonic generator laser ranges from 500 nm to 550 nm.

In some embodiments of the method a variation in polydispersity index (PDI) of the polymeric stent represented by the following Equation 1 is 20% or less:

$$\text{Variation in Polydisperity Index}(\%) = \frac{B-A}{A} \times 100 \quad \text{(Equation 1)}$$

wherein, in Equation 1: A is a polydispersity index of a polylactic acid tube before a pattern is formed; and B is a polydispersity index of the polymeric stent after the pattern is formed.

In some embodiments of the method a variation in average molecular weight of the polymeric stent represented by the following Equation 2 is 20% or less:

$$\text{Variation in Average Molecular Weight}(\%) = \frac{C-D}{C} \times 100 \quad \text{(Equation 2)}$$

wherein, in Equation 2: C is an average molecular weight of a polylactic acid tube before a pattern is formed; and D is an average molecular weight of the polymeric stent after the pattern is formed.

In some embodiments of the method the polymeric stent has a target diameter and is capable of withstanding expansion of up to 1 mm beyond the target diameter without forming fractures or cracks in the stent, as measured by a scanning electron microscope (SEM).

In some embodiments the method further comprises applying to the polymeric stent a composition effective to prevent restenosis of a lumen in a body vessel; and radially compressing the polymeric stent.

In some embodiments the method further comprises forming a groove or a hole on at least one of the struts of the linker portion; and affixing a radiomarker to the groove or the hole.

In some embodiments, the polymeric stent can be manufactured by any one of the foregoing methods.

In some embodiments a polydispersity index of the polymeric stent ranges from 1 to 2, 1 to 1.7, 1 to 1.6.

The present disclosure also provides a polymeric stent, the stent comprising: a pattern of repeating units comprising a plurality of unit cells, wherein each unit cell has a V-shaped configuration and comprises a first hinge portion having a first end and a second end, wherein the first hinge portion is bent inwardly to the unit cell and a second hinge portion having a first end and a second end, wherein the second hinge portion is facing the first hinge portion and bent outwardly from the unit cell; and a linker portion extended outwardly from a bent portion of the second hinge portion; wherein the repeating units are disposed such that an end of a linker portion of one repeating unit is connected to a bent portion of a first hinge portion of an adjacent repeating unit, or the first end of a first hinge portion and the first end of a second hinge portion of one repeating unit are connected to an end of a first hinge portion and an end of a second hinge portion of the adjacent repeating unit, respectively; wherein the thickness of the unit cell and the strut of the linker portion is 80 to 160 μm; wherein the pattern is formed on a polymer tube using a laser.

In certain embodiments, the polymer tube is formed using a second harmonic generator laser in which a wavelength ranging from 940 nm to 1552 nm is converted. In other embodiments, the second harmonic generator laser is a laser in which a wavelength ranging from 1000 nm to 1100 nm is converted. In some embodiments, the polymer tube is made of polylactic acid. In some embodiments a pulse width of the second harmonic generator laser is 10 ps or less. In some embodiments a pulse width of the second harmonic generator laser is 1 ps or less.

In some embodiments of the polymeric stent an output wavelength of the second harmonic generator laser ranges from 470 nm to 776 nm. In some embodiments an output wavelength of the second harmonic generator laser ranges from 500 nm to 550 nm.

In some embodiments of the polymeric stent has a target diameter and is capable of withstanding expansion of up to 1 mm beyond the target diameter without forming fractures or cracks in the stent, as measured by a scanning electron microscope (SEM).

In certain embodiments of the polymeric stent, a variation in polydispersity index (PDI) represented by the following Equation 1 is 20% or less:

$$\text{Variation in Polydisperity Index(\%)} = \frac{B-A}{A} \times 100\% \qquad \text{(Equation 1)}$$

wherein, in Equation 1: A is a polydispersity index of a polymeric stent before a pattern is formed; and B is a polydispersity index of the polymeric stent after the pattern is formed.

In some embodiments a polydispersity index of the polymeric stent, in which the pattern is formed, ranges from 1 to 2.

In some embodiments a variation in average molecular weight of the polymeric stent represented by the following Equation 2 is 20% or less:

$$\text{Variation in Average Molecular Weight(\%)} = \qquad \text{(Equation 2)}$$
$$\frac{C-D}{C} \times 100\%$$

wherein, in Equation 2: C is an average molecular weight of a polymeric stent before a pattern is formed; and D is an average molecular weight of the polymeric stent after the pattern is formed.

In some embodiments a polymeric stent comprises a pattern of repeating units comprising a plurality of unit cells, wherein each unit cell has a V-shaped configuration and comprises a first hinge portion having a first end and a second end, wherein the first hinge portion is bent inwardly to the unit cell and a second hinge portion having a first end and a second end, wherein the second hinge portion is facing the first hinge portion and bent outwardly from the unit cell; and a linker portion extended outwardly from a bent portion of the second hinge portion; wherein the repeating units are disposed such that an end of a linker portion of one repeating unit is connected to a bent portion of a first hinge portion of an adjacent repeating unit, or the first end of a first hinge portion and the first end of a second hinge portion of one repeating unit are connected to an end of a first hinge portion and an end of a second hinge portion of the adjacent repeating unit, respectively; wherein the thickness of the unit cell and the strut of the linker portion is 80 to 160 μm; wherein the pattern is formed on a polymer tube using a laser; wherein a pattern is formed using a second harmonic generator laser in which a wavelength ranging from 940 nm to 1552 nm is converted; and wherein a variation in average molecular weight represented by the following Equation 2 is 20% or less:

$$\text{Variation in Average Molecular Weight(\%)} = \qquad \text{(Equation 2)}$$
$$\frac{C-D}{C} \times 100\%$$

wherein, in Equation 2, C is an average molecular weight of a polymeric stent before a pattern is formed; and D is an average molecular weight of the polymeric stent after the pattern is formed.

In certain embodiments, the polymer tube is formed using a second harmonic generator laser in which a wavelength ranging from 940 nm to 1552 nm is converted. In other embodiments, the second harmonic generator laser is a laser in which a wavelength ranging from 1000 nm to 1100 nm is converted. In some embodiments, the polymer tube is made of polylactic acid. In some embodiments a pulse width of the second harmonic generator laser is 10 ps or less. In some embodiments a pulse width of the second harmonic generator laser is 1 ps or less.

In some embodiments of the polymeric stent an output wavelength of the second harmonic generator laser ranges from 470 nm to 776 nm. In some embodiments an output wavelength of the second harmonic generator laser ranges from 500 nm to 550 nm.

In some embodiments of the method the polymeric stent has a target diameter and is capable of withstanding expansion of up to 1 mm beyond the target diameter without forming fractures or cracks in the stent, as measured by a scanning electron microscope (SEM).

BRIEF DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numerals, and where:

In FIG. 3A, the polymeric stent is crimped. In FIG. 3B, the polymeric stent is expanded.

FIG. 4A shows a form of the unit cell when the interior angle 400 of the second hinge portion is about 90°, and FIG. 4B shows a form of the unit cell when the interior angle 400 of the second hinge portion is about 160°.

In FIG. 5A, the thickness of the strut is about 80 μm. In FIG. 5B, the thickness of the strut is about 120 μm.

DETAILED DESCRIPTION

Figure 1:
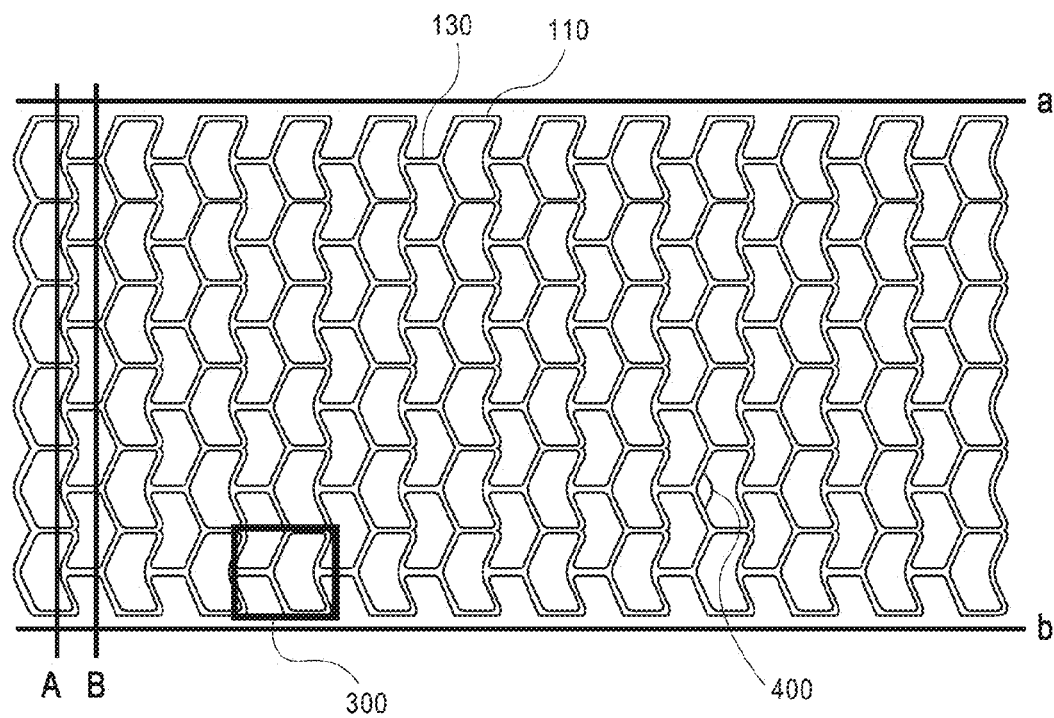
FIG. 1 is a schematic view of a pattern of a polymeric stent according to an exemplary embodiment of the present invention.

The following discussion provides examples of embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Those of skill in the art will recognize that the described embodiment are examples of possible configurations of the invention, and are not intended to be limiting to the scope of the invention. Accordingly, the drawings and descriptions contained herein are to be regarded as illustrative of the invention as set forth in the accompanying claims.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The present disclosure provides methods for manufacturing polymeric stents by forming a pattern on a polymer tube with a laser, where the pattern formed on the polymer tube comprises a plurality of repeating units comprising a plurality of unit cells, each having a V-shaped configuration as described herein.

In certain embodiments, the method comprises manufacturing the polymeric stent by forming a pattern on a polylactic acid tube with a second harmonic generator laser.

A second harmonic generator laser refers to a laser of which the wavelength is divided in half using a second harmonic generator (SHG), a technique first described by Franken et al. (*Physical Review Letters* 7(4): 118 (1961)). In general, the technique operates by passing a coherent light such as a laser emission through a non-linear crystal and then a prism to generate a second harmonic wave and a residual wave. In the present disclosure it is the second harmonic wave that is used to form the pattern in the polymeric stent. Thus, in an exemplary embodiment of the present specification, the pattern may be formed on the polylactic acid tube using a second harmonic generator laser to convert an initial input wavelength ranging from about 940 nm to about 1552 nm to a lower output wavelength.

Specifically, the pattern may be formed on the polylactic acid tube using a laser in which the wavelength of a laser having an input wavelength ranging from about 940 to about 1552 nm, is divided in half through a second harmonic generator (SHG). More specifically, the pattern may be formed on the polylactic acid tube using a laser in which the wavelength of a laser having an input wavelength ranging from about 1000 nm to about 1100 nm is divided in half via a second harmonic generator (SHG).

As used herein, the specific type of laser having the wavelength is not particularly limited as long as the emission wavelength is within a range from about 940 nm to about 1552 nm. For example, exemplary lasers may be any one of neodymium-doped laser, ytterbium-doped laser, erbium-doped laser and hybrid fiber laser.

In some embodiments, the pattern may be formed on a polylactic acid tube using a second harmonic generator laser in which an input wavelength ranging from about 940 nm to about 1552 nm is converted, resulting in an output wavelength ranging from about 470 nm to about 776 nm.

In some embodiments, the pattern may be formed on a polylactic acid tube using a second harmonic generator laser in which an input wavelength ranging from about 1000 nm to about 1100 nm is converted, resulting in an output wavelength ranging from about 500 nm to about 550 nm.

Recently, the demand has increased for polymeric stents manufactured using a biodegradable polymer that will degrade in vivo. In this case, a biodegradable polymer such as polylactic acid is sensitive to an external environment such as heat, moisture and light. The molecular weight of the biodegradable polymer greatly affects the performance characteristics of a polymeric stent made from the biodegradable polymer, including, for example, the mechanical strength and biodegradation rate of the polymeric stent.

Accordingly, the molecular weight of the biodegradable polymer needs to be selected in order to ensure adequate mechanical strength of the polymeric stent, while optimizing the rate of biodegradation. For example, one consideration in designing a process of manufacturing the polymeric stent will be to provide for variability in sensitivity to heat, moisture and the like, while the molecular weight of the biodegradable polymer material remains unchanged.

For example, in some embodiments of a method of manufacturing a polymeric stent, forming a pattern on a polymeric tube can be done using a laser. However, when prior art methods of processing a biodegradable polymeric stent are performed using a laser having a long pulse length output, it has been observed that the polymer material can overheat and eventually become molten. This can result in a heat-affected zone within the stent where the molecular weight of the biodegradable polymer material has been decreased by the effects of laser heating. This in turns leads to degradation of the mechanical performance of the material in the affected area, for example reduced strength.

Little is known about the effect of using ultra-short pulse laser outputs, or changing laser wavelength on the properties of biodegradable polymers suitable for use in producing polymeric stents as described herein. Therefore, in the present case, the inventors have studied the change in properties of the biodegradable polymeric stent in response to processing with lasers having an ultra-short pulse length, and shorter wavelengths. It has been discovered that when a pattern is formed on a polylactic acid tube using a second harmonic generator laser having a wavelength ranging from about 470 nm to about 776 nm, thermal injury of the polylactic acid polymer at the cut surface of the polylactic acid tube is significantly reduced. The result is a method of using SHG laser radiation to form stents from polymeric tubes, while retaining the mechanical properties of the polymer material.

It has been found that when a pattern is formed on a polylactic acid tube using a second harmonic generator laser having an output wavelength ranging from about 470 nm to about 776 nm, there is a further advantage in that degradation of the polylactic acid polymer at the cut surface of the polylactic acid tube is reduced as compared to prior art methods of laser processing.

In the present specification, when a pattern is formed on a polylactic acid tube using the second harmonic generator laser having a wavelength ranging from about 470 nm to about 776 nm, there is still a further advantage in that the change in molecular weight of the polylactic acid polymer at the cut surface of the polylactic acid tube is reduced as compared to prior art methods of laser processing.

Using the laser processing methods as described herein, a variation in polydispersity index (PDI) of the polymeric stent, represented by the following Equation 1, may be 20% or less. Dispersity in a material is a measure of the relative homogeneity of molecules or particles within a mixture.

$$\text{Variation in Polydisperity Index}(\%) = \frac{B-A}{A} \times 100 \quad \text{Equation 1}$$

In Equation 1,
A is a polydispersity index of a polylactic acid tube before a pattern is formed on the polylactic acid tube, and
B is a polydispersity index of the polymeric stent after the pattern is formed on the polylactic acid tube.

Furthermore, using the laser processing methods as described herein, variation in the average molecular weight of the polymeric material comprising the stent, which is represented by the following Equation 2, may be 20% or less.

$$\text{Variation in Average Molecular Weight}(\%) = \frac{C-D}{C} \times 100 \quad \text{Equation 2}$$

In Equation 2,
C is an average molecular weight of a polylactic acid tube before a pattern is formed on the polylactic acid tube, and
D is an average molecular weight of the polymeric stent after the pattern is formed on the polylactic acid tube.

As used herein, the term "variation in average molecular weight" refers to a variation in number average molecular weight or a variation in mass average molecular weight.

The specification provides a method for manufacturing a polymeric stent in which a pattern is formed using a second harmonic generator laser where a wavelength ranging from about 940 nm to about 1552 nm is converted, and a variation in polydispersity index (PDI) is 20% or less as measured by Equation 1.

The polydispersity index of the polymeric stent produced using a second harmonic generator laser where a wavelength ranging from about 940 nm to about 1552 nm is converted, may range from 1 to 2, 1 to 1.9, 1 to 1.8, 1 to 1.7, 1 to 1.6, or 1 to 1.5.

The specification also provides a method for manufacturing a polymeric stent in which the pattern of the polymeric stent is formed using a second harmonic generator laser in which an initial input wavelength ranging from about 940 nm to about 1552 nm is converted, a variation in PDI is 20% or less as measured by Equation 1, and a variation in average molecular weight is 20% or less as measured by Equation 2.

The specification also provides a method for manufacturing a polymeric stent in which the pattern of the polymeric stent is formed using a second harmonic generator laser in which an initial input wavelength ranging from about 940 nm to about 1552 nm is converted and a variation in average molecular weight is 20% or less as measured by Equation 2.

Using the laser processing methods as described herein, a polydispersity index of the polymeric stent on which the pattern is formed may range from 1 to 2, 1 to 1.9, 1 to 1.8, 1 to 1.7, 1 to 1.6, or 1 to 1.5.

As used herein, the term "polydispersity index" means a value obtained by dividing a mass average molecular weight by a number average molecular weight. A number approaching 1.0 is indicative of narrow dispersion of molecular weight of the polymeric material.

Using the laser processing methods as described herein, a pulse width of a second harmonic generator laser can be 10 picosecond (ps) or less. Specifically, a pulse width of a second harmonic generator laser may be 1 picosecond (ps) or less. If necessary, a pulse width of a second harmonic generator laser may be 900 femtosecond (fs) or less. The lower limit of the pulse width of the second harmonic generator laser is not particularly limited as long as the value is 10 ps or less, but may be, for example, 1 fs or more.

As used herein, the term, "pulse" refers to a waveform in which the amplitude appears with an impact only within a short time at a constant interval, and a width of the pulse means an interval between a time when the amplitude of the pulse becomes ½ in a rise time and a time when the amplitude of the pulse becomes ½ in a fall time.

Using the laser processing methods as described herein, a width of the pulse of the laser may range from about 1 fs to about 900 fs, either before or after being converted into the second harmonic wave.

Using the laser processing methods as described herein, a repetition rate of the laser may range from about 2 kHz to about 200 kHz, either before or after being converted into the second harmonic wave.

Using the laser processing methods as described herein, the power of the laser may range from about 0.1 W to about 10 W, either before or after being converted into the second harmonic wave.

Using the laser processing methods as described herein, a spot size of the second harmonic generator laser may range from about 1 μm to about 50 μm.

In some embodiments of the laser processing methods as described herein, the method may include manufacturing a polylactic acid tube before forming the pattern. Manufacturing of the polylactic acid tube may include: manufacturing the polylactic acid tube by extruding a molten polylactic acid polymer, and then expanding the extruded polylactic acid tube to a pre-determined diameter. Since the extent to which the diameter of the polylactic acid tube is expanded determines the ultimate diameter of the polylactic acid tube in the forming of the pattern, the diameter of the expanded polylactic acid tube can be the same as that of the polylactic acid tube prepared for the forming of the pattern. In selecting a diameter of the polylactic acid tube to be formed, the outer diameter of the expanded polylactic acid tube may be the same as or smaller than the inner diameter of the blood vessels, or other body vessels where the stent is intended to be implanted.

The inner diameter of the blood vessels may vary depending on the blood vessel into which the polymeric stent is inserted. For example, when the blood vessel into which the polymeric stent is inserted is a coronary artery, the diameter of the blood vessel may range from about 2.5 mm to about 4.0 mm.

The outer diameter of the expanded polylactic acid tube may range from about 30% to about 100% of the inner diameter of the blood vessel. If some embodiments, the outer diameter of the expanded polylactic acid tube may range from about 40% to about 70% of the inner diameter of the blood vessel.

In addition to the polymeric material comprising the bulk of a stent, in some embodiments methods of stent manufacturing may further include applying a composition on the surface of the polymeric stent that is effective to prevent restenosis. The thickness of a composition applied on the polymeric stent can range from about 2 μm to about 30 μm. A composition for preventing restenosis may be applied on a part, or all, of the surface of the polymeric stent. In some embodiments of the method, a composition for preventing restenosis may be applied on an outer side surface and/or an inner side surface of the polymeric stent.

The precise composition used for preventing restenosis is not limiting to the scope of the invention. As long as the composition is effective to prevent restenosis, it is expected to generally be compatible with polymeric stents manufactured according to the methods described herein. For example, in some embodiments the composition for preventing restenosis may include a Rapamycin-based compound. For example, a Rapamycin-based compound may include one or more of Sirolimus, Everolimus, Biolimus, Zotarolimus and the like.

In some embodiments, a composition for preventing restenosis may further include a second polymer and a solvent. The second polymer is not particularly limited as long as it imparts adhesive properties to the surface of the polymeric stent. For example, in some embodiments, the second polymer may be the same as or similar to the polymer constituting the polymeric stent. For example, when a material for the polymeric stent includes a polylactic acid-based polymer, a second polymer included in the composition for preventing restenosis may also include a polylactic acid-based polymer.

Furthermore, the choice of solvent is not particularly limited, and may be selected among those well know to those skilled in the art. For example, the solvent may include one or two or more selected from acetone, methanol and ethanol. The concentration of the solute material, other than the solvent in the composition for preventing restenosis, may range from about 0.1% by weight to about 5% by weight.

In some embodiments of the present method, the method may further include compressing the polymeric stent. In some cases, compression can be performed such that the form of the circular cross-sectional surface of the polymeric stent is maintained. Specifically, compressing the stent can be accomplished by applying a uniform radial compression force to the polymeric stent. A radial direction refers to a vector from the circumference of the circle to the center of a circle on the cross-sectional surface, the vector being perpendicular to the longitudinal direction of the polymeric stent.

The temperature during compression of the stent may range from body temperature to the glass transition temperature. For example, temperatures during compression may be performed over a range of temperatures ranging from about 36° C. to about 60° C.

During compression, the polymeric stent may be compressed uniformly in all radial directions using a crimping head heated to a temperature that ranges from about normal body temperature to about glass transition temperature of the polymer forming the stent.

Prior to compressing a polymeric stent, a balloon may be inserted into the inside of the polymeric stent, and then the polymeric stent may be compressed. The balloon is configured for use to permit later expansion of the stent at the treatment site in the body. The outer diameter of the compressed polymeric stent can range from about 1 mm to about 1.6 mm. The compressed stent and balloon combination can then be packaged for delivery for use in treatment of a patient.

In placing the stent, a delivery device is used to position the polymeric stent in the compressed state at a desired treatment site in a body vessel. Once the stent is in place within the body vessel, inflating the balloon expands the polymeric stent. Once the stent has been expanded to the desired size, the delivery device can be detached from the polymeric stent and removed from the patient, leaving the polymeric stent behind to support the body vessel at the treatment site.

Figure 12:
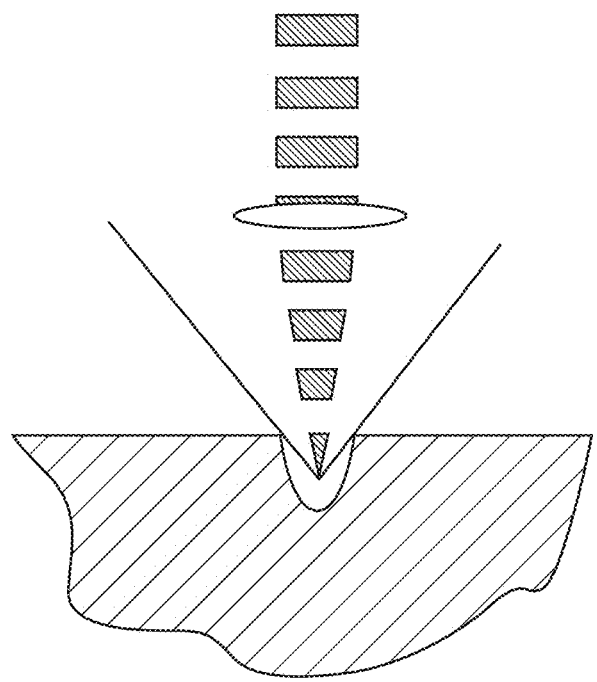
FIG. 12 illustrates an exemplary embodiment in which a groove is formed on the surface of an embodiment of a polymeric stent using ultra-short pulse laser.

Methods for manufacturing a polymeric stent may further include forming a groove or a hole on at least one of the struts of the polymeric stent on which the pattern is formed, and affixing a radiomarker to the groove or the hole. In the forming of the groove or the hole, it is possible to use an ultra-short pulse laser to form a groove which does not pass through the strut as illustrated in FIG. 12 or form a hole which passes through the strut.

In the forming of the pattern, the pattern formed on the surface of the polymeric stent is not particularly limited, and a pattern generally used in the art may be adopted.

In a preferred embodiment, the polymeric stent manufactured by the laser processing methods disclosed herein has the structure and pattern as set forth in FIG. 1. As shown in FIG. 1, the polymeric stent comprises: a repeating unit including a unit cell having a V or chevron shape and including a first hinge portion bent inwardly to the unit cell and a second hinge portion facing the first hinge portion and bent outwardly from the unit cell; a linker portion extended outwardly from a bent portion 270 of the second hinge portion.

In some embodiments, the repeating units may be disposed such that an end of a linker portion 150 of one repeating unit is connected to a bent portion 220 of a first hinge portion of another adjacent repeating unit, or an end of a first hinge portion 210 and an end of a second hinge portion 220 of one repeating unit may be disposed so as to be connected to an end of a first hinge portion and an end of a second hinge portion of the adjacent other repeating unit, respectively.

The polymeric stent according to an exemplary embodiment includes three or more repeating units, the repeating units may be disposed such that an end of a linker portion of one repeating unit is connected to a bent portion of a first hinge portion of another adjacent repeating unit, and an end of a first hinge portion and an end of a second hinge portion of one repeating unit may be disposed so as to be connected to an end of a first hinge portion and an end of a second hinge portion of another adjacent repeating unit, respectively.

The polymeric stent may be manufactured by disposing one or more repeating units in a row. In an exemplary embodiment, the polymeric stent can take the form of a tube, with 4 to 15 repeating units disposed circumferentially in order to form the tube.

In some embodiments, the polymeric stent may be formed in the form of a cylinder by connecting one end of the pattern of the polymeric stent manufactured by repeating the repeating unit of the present invention to the other end thereof.

In an exemplary embodiment, when an end of a first hinge portion and an end of a second hinge portion of one repeating unit are disposed so as to be connected to an end of a first hinge portion and an end of a second hinge portion of another adjacent repeating unit, respectively, a line in which one or more unit cells are consecutively disposed side by side and a line in which one or more linker portions among the repeating units are disposed spaced apart from each other are formed. A line of the unit cell is defined as the (A) row, and the line of the linker portion is defined as the (B) row.

In an exemplary embodiment, when the repeating unit is repeatedly disposed in one direction and in the other direction vertical to the one direction, a closed figure may be formed even at the (B) row, which is the line of the linker portion.

In an exemplary embodiment, when the repeating unit is repeatedly disposed in one direction and in the other direction vertical to the one direction, a closed figure in the shape of a V or chevron, and which is positioned in a direction opposite to a unit cell having a shape of a closed figure that is shaped like a V or chevron at the (A) row, may be formed at the (B) row which is a line of the linker portion.

In an exemplary embodiment, when one end (a) of the pattern of the polymeric stent is connected to the other end (b) thereof, open figures at both ends of the (B) row may be connected to each other to form a closed figure.

In an exemplary embodiment, when one end (a) of the pattern of the polymeric stent is connected to the other end (b) thereof, open figures at both ends of the (B) row may be connected to each other to form a closed figure shaped like a V or chevron, which is positioned in a direction opposite to the unit cell having a shape of a closed figure shaped like a V or chevron at the (A) row thereof.

In the repeating unit of an exemplary embodiment, the length of the linker portion may be shorter than the distance between the bent portion of the first hinge portion and the bent portion of the second hinge portion.

Accordingly, the unit cell having a shape of a closed figure that is shaped like a V or chevron at the (A) row may be larger than a closed figure shaped like a V or chevron at the (B) row, which is formed by the linker portion. In addition, in a longitudinal direction of the linker portion, the height of the unit cell having a shape of a closed figure shaped like a V or chevron at the (A) row may be larger than the height of a closed figure shaped like a V or chevron at the (B) row, which is formed by the linker portion.

In the repeating unit of an exemplary embodiment, the length of the linker portion may be longer than the distance between the bent portion of the first hinge portion and the bent portion of the second hinge portion.

Accordingly, the unit cell having a shape of a closed figure shaped like a V or chevron at the (A) row may be smaller than a closed figure shaped like a V or chevron at the (B) row, which is formed by the linker portion. Furthermore, in a longitudinal direction of the linker portion, the height of the unit cell having a shape of a closed figure shaped like a V or chevron at the (A) row may be smaller than the height of a closed figure shaped like a V or chevron at the (B) row, which is formed by the linker portion.

In the polymeric stent according to an exemplary embodiment, a corner and an end of one repeating unit are connected to a corner and an end of another unit cell. That is, in the polymeric stent according to an exemplary embodiment, a repeating unit does not have a corner or end, and which is not connected to each other.

The polymeric stent of the present invention does not have a corner or end that is not connected to each other, and thus is advantageous in that the polymeric stent of the present invention has a relatively higher mechanical strength than that of a polymeric stent having a different design but is formed of a strut having the same thickness.

In other polymeric stents having a corner or end that is not connected to each other, the unconnected corner or end fails to serve to support the polymeric stent. Thus the polymeric stent of the present invention, which does not have a corner or end that is not connected to each other, has an unexpectedly high mechanical strength.

For example, polymeric stents manufactured according to the methods of the present disclosure and having the V-shaped configuration described above have significantly greater radial strength with respect to strut thickness as compared to stents that have other configurations (e.g., W-shaped). As a result, polymeric stents as described herein having a V-shaped cell, and having no corner or end that is not connected to each other, provide an additional advantage in that they can be over-expanded (or over-inflated) past the target diameter to a greater extent than stents with other configurations. Without intending to be bound by any theory, this appears to be primarily due to the different distribution of forces in the V-shaped cells of the polymeric stent as compared to other configurations.

With a polylactic acid stent having V-shaped cell configuration, the forces imposed on strut junctions upon expansion are significantly lessened, reducing the likelihood of stress fracture in the struts. For example, certain polylactic acid stents with a W-shaped configuration can be expanded past the target diameter only by about 0.5 mm before stent fracture or significant loss of radial strength occurs. However, a similar-sized polylactic acid stent with V-shaped cell configuration, as described herein, can be expanded past the target diameter by as much as 1.0 mm before stent fracture (as measured by SEM) or significant loss of radial strength occurs.

As used herein, "target diameter" means the intended outer diameter of a stent before implantation into a vessel.

It is understood in the art that polymeric materials used to manufacture biodegradable stents have different properties, such as lower strength to weight ratios, than the materials used to manufacture metallic stents. As a result, it is understood in the art that struts in polymeric stents generally must be made thicker and wider than struts in metallic stents to have the necessary strength, e.g., to maintain the patency of the lumen of a vessel.

However, the polymeric stent of the present invention does not have a corner or end which is not connected to each other, and thus is advantageous in that a mechanical strength sufficient to maintain vessel patency may be imparted with a relatively thin strut, contrary to the general understanding in the art.

The polymeric stent of the present invention is thus advantageous, in part, because it may be manufactured with a relatively thin strut while retaining both the strength and flexibility sufficient to maintain patency of the lumen of a vessel.

In the polymeric stent according to an exemplary embodiment, the thinner the thickness of the strut, the smaller the size of the repeating unit becomes, thereby increasing the number of repeating units per the same area. In this way the mechanical strength of the polymeric stent may be maintained even while using relatively thin struts, the dimensions of which were not previously attainable with polymeric stents.

Further, other polymeric stents suffer from the disadvantage in that after the polymeric stent is implanted into the blood vessels, the corner which is not connected to each other may hamper the blood stream within the blood vessels resulting in formation of hematomas and the like. However, the polymeric stent of the present invention does not have a corner or end that is not connected to each other, and thus the aforementioned problem may be alleviated.

In the present invention, the corner means a point that is positioned at an end and a bent portion of the first hinge portion, an end and a bent portion of the second hinge portion, and an end of the linker portion in one repeating unit. In an exemplary embodiment, the interior angle 400 of the second hinge portion may be about 100° or more. In an exemplary embodiment, the interior angle 400 of the second hinge portion may be from about 90° to about 160°.

Figure 2:
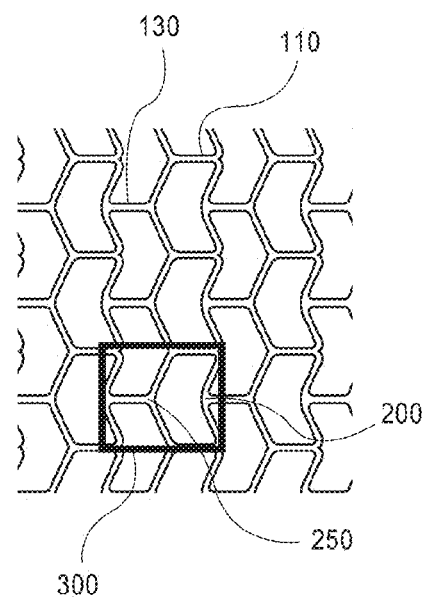
FIG. 2 is an enlarged view of FIG. 1.

In an exemplary embodiment, in the repeating unit, the area of a rectangle the perimeter of which passes through both ends of the first hinge portion, both ends of the second hinge portion and an end of the linker portion may range from about 0.1 mm² to 45 mm² and from about 0.13 mm² to 44.38 mm². It will be understood that the area of the rectangle means an area of a region occupied by one unit cell and a linker portion thereof. That is, the area of the rectangle means an area of the rectangle that defines a region of one unit cell and a linker portion thereof, as illustrated in FIGS. 1 and 2.

In an exemplary embodiment, the repeating unit may include a strut of the unit cell, which is a line that forms the closed figure shaped like a V or chevron of the unit cell and a strut of the linker portion, which is a line that forms the linker portion.

In an exemplary embodiment, the repeating unit 300 includes a strut of the unit cell, which is a line that forms the closed figure shaped like a V or chevron of the unit cell and a strut of the linker portion, and which is a line that forms the linker portion, and in the polymeric stent, the area of the strut of the unit cell and the strut of the linker portion in the repeating unit may be from about 5 to 46%, based on the area of the rectangle which passes through both ends of the first hinge portion, both ends of the second hinge portion, and an end of the linker portion.

If necessary, the area of the strut of the unit cell and the strut of the linker portion in the repeating unit may be from about 15 to 40% and from about 25 to 35%, based on the area of the rectangle which passes through both ends of the first hinge portion, both ends of the second hinge portion, and an end of the linker portion.

In the repeating unit, the area of the rectangle that passes through both ends of the first hinge portion, both ends of the second hinge portion and an end of the linker portion means an area of a region that one unit cell and a linker portion thereof occupy, and the area of the strut of one unit cell and the strut of the linker portion means an area that the line of each strut occupies.

In an exemplary embodiment, the thickness of the strut of the unit cell and the strut of the linker portion may be from about 80 to 100 µm, 80 to 120 µm, 80 to 140 µm, or 80 to 160 µm.

At this time, the thickness of the strut means a length thereof in a direction that is vertical to the longitudinal direction. That is, the thickness of the strut means the line width of the strut.

In an exemplary embodiment, when the polymeric stent is a tube type, the diameter of the polymeric stent may be from about 2 to 8 mm.

In certain embodiments, when the polymeric stent is a tube type, in a cross-section, which is a direction that is vertical to the axis, the diameter of the polymeric stent means a length of a line segment that connects two points on the cross-section so as to pass through the center of the cross-section.

As used herein, the diameter of the polymeric stent means a diameter of a polymeric stent formed by connecting one end of the pattern of the polymeric stent with the other end thereof.

In some embodiments, the polymeric stent may include a biodegradable polymer. The biodegradable polymer is not particularly limited as long as the polymer may be degraded in vivo. For example, the biodegradable polymer may be a synthetic biodegradable polymer or natural biodegradable polymer.

A synthetic biodegradable polymer may be a polymer selected from polyglycolide, polylactide, poly p-dioxanone, polycaprolactone, trimethylene carbonate, polyhydroxyalkanoates, polypropylene fumarate, polyortho esters, other polyester, polyanhydride, polyphosphazenes, polyalkylcyanoacrylate, poloxamers, and polyamino L-tyrosine, or a copolymer thereof or mixtures thereof. A natural biodegradable polymer may be a material selected from modified polysaccharides, oxidized cellulose, gelatin, and collagen, or a mixture of one or more thereof. In one embodiment, the biodegradable polymer comprises a polylactide.

A stent as described herein is an expandable medical prosthetic device, intended for implantation within body vessels of humans to treat a variety of medical applications and serves to maintain the form of the body vessel and patency of the lumen of the body vessel. For example, stents as described herein may be used as intravascular stents for treating cardiovascular stenoses, for maintaining openings in the urinary, biliary, tracheobronchial, esophageal, and renal tracts, and inferior vena cava, and the like.

The stent of the present invention can be delivered to a treatment site through various body vessels by using a delivery device. After the stent is positioned at the treatment site, the delivery device is actuated to release the stent and the stent is mechanically expanded, for example, with the aid of an inflatable balloon, within the body vessel. The delivery device is then detached from the stent, and the stent remains within the body vessel at the treatment site as an implant.

The polymeric stent according to an exemplary embodiment provides additional advantages in that the stent is less distorted by resistance when the polymeric stent is implanted into blood vessels or lumens of other body vessels.

The polymeric stent according to an exemplary embodiment provides further advantages in that the patterns thereof are not entangled with each other when the polymeric stent is expanded as occurs with other wire stent designs.

When the polymeric stent of the present invention is manufactured from a biodegradable polymer, the stent remains within the body vessel at the treatment site, and is naturally degraded after a certain time, eventually disappearing. In some embodiments, a polymeric stent can be manufactured from materials that will completely degrade over a period of about two years in the body.

In the polymeric stent according to an exemplary embodiment, the repeating unit may be formed by processing a polymeric tube using a laser. Specifically, the repeating unit of the present invention may be formed on the side surface of the polymeric tube.

The present invention further provides a method for manufacturing a polymeric stent, the method comprising: forming a repeating unit including a unit cell having a shape of a closed figure that looks like a V or chevron and including a first hinge portion bent inwardly to the unit cell and a second hinge portion facing the first hinge portion and bent outwardly from the unit cell; and a linker portion extended outwardly from a bent portion of the second hinge portion; and disposing the repeating units, such that an end of a linker portion of one repeating unit is connected to a bent portion of a first hinge portion of another adjacent repeating unit, or forming the repeating units continuously such that an end of a first hinge portion and an end of a second hinge portion of one repeating unit are connected to an end of a first hinge portion and an end of a second hinge portion of another adjacent repeating unit, respectively.

In an exemplary embodiment, the repeating unit may be formed in a polymer material using a laser.

In an exemplary embodiment, the repeating unit may be formed on the side surface of the polymeric tube. As used herein, a tube means one having a long axial length relative to width.

Figure 3A:
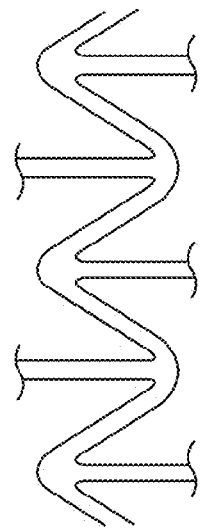
FIGS. 3A and 3B illustrate the shape of a pattern of the polymeric stent according to an exemplary embodiment of the present invention.
Figure 3B:
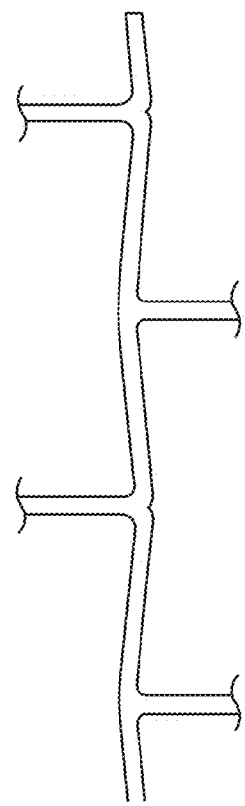
Figure 4A:
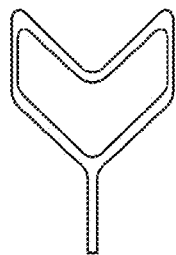
FIGS. 4A and 4B illustrate the change in shape of the unit cell according to the interior angle of the second hinge portion of the polymeric stent according to an exemplary embodiment of the present invention.
Figure 4B:
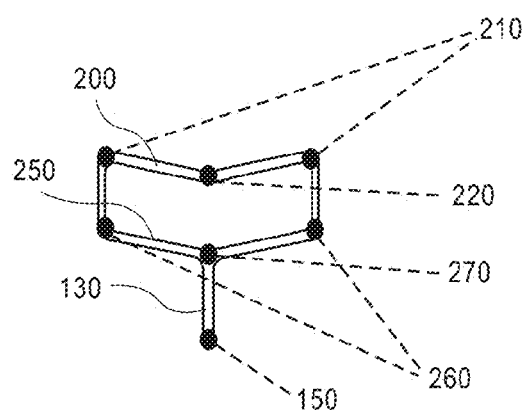
Figure 5A:
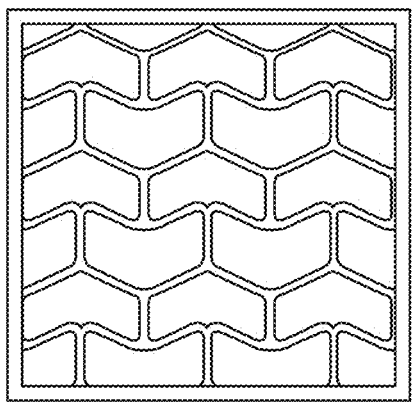
FIGS. 5A and 5B illustrate the change in pattern according to the thickness of the strut of the polymeric stent according to an exemplary embodiment of the present invention.
Figure 5B:
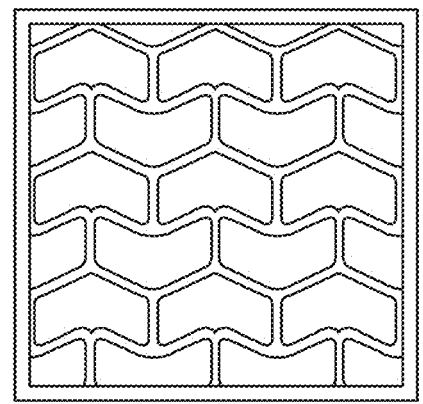

FIG. 1 is a schematic view of a pattern of a polymeric stent according to an exemplary embodiment. FIG. 2 depicts and enlarged view of FIG. 1. FIGS. 3A-B illustrate the shape of the pattern of a polymeric stent according to an exemplary embodiment in each state of (a) when the polymeric stent is crimped, or (b) when the polymeric stent is expanded, respectively. FIGS. 4A-B illustrate the change in shape of the unit cell according to the interior angle of the second hinge portion of the polymeric stent according to an exemplary embodiment. FIGS. 5A-B illustrate the change in pattern according to the thickness of the strut of a polymeric stent according to an exemplary embodiment.

As illustrated in FIGS. 1 and 2, an embodiment of a polymeric stent includes a unit cell 110 having a shape of a close figure shaped like a V or chevron, and including a first hinge portion 200 bent inwardly to the unit cell 110 and a second hinge portion 250 facing the first hinge portion 200 and bent outwardly from the unit cell; and a repeating unit 300 including a linker portion 130 extended outwardly from a bent portion of the second hinge portion.

In an exemplary embodiment of a polymeric stent, as illustrated in FIGS. 1 and 2, the repeating units 300 may be disposed such that an end of a linker portion of one repeating unit is connected to a bent portion of a first hinge portion of another adjacent repeating unit, or an end of a first hinge portion and an end of a second hinge portion of one repeating unit are connected to an end of a first hinge portion and an end of a second hinge portion of another adjacent repeating unit, respectively.

Yet another embodiment of a polymeric stent includes three or more repeating units, where the repeating units may be disposed such that an end of a linker portion of one repeating unit is connected to a bent portion of a first hinge portion of another adjacent repeating unit, and an end of a first hinge portion and an end of a second hinge portion of one repeating unit are connected to an end of a first hinge portion and an end of a second hinge portion of further another adjacent repeating unit, respectively.

As illustrated in FIGS. 1 and 2, an embodiment of a polymeric stent may be manufactured by disposing one or more of the repeating unit 300 in a row.

In another embodiment, 4 to 15 repeating units may be disposed circumferentially to produce a tube-shaped polymeric stent.

As illustrated in FIG. 1, a polymeric stent may be shaped in the form of a cylinder by connecting one end (a) of the pattern of the polymeric stent manufactured by repeating the repeating unit 300 of the present invention to the other end (b) thereof.

Further, and as illustrated in FIG. 1, a line disposed such that an end of a first hinge portion and an end of a second hinge portion of one unit cell are connected to an end of a first hinge portion and an end of a second hinge portion of another adjacent unit cell, respectively, is defined as the (A) row. Similarly, a line of the linker portion 130 formed according to the disposition of the unit cell is defined as the (B) row.

As is also illustrated in FIG. 1, when the repeating unit 300 is repeatedly disposed in one direction and in the other direction vertical to the one direction, a closed figure may be formed even at the (B) row, which is the line of the linker portion.

Similarly, when the repeating unit 300 is repeatedly disposed in one direction and in the other direction vertical to the one direction, a closed figure having a V or chevron shape, which is positioned in a direction opposite to the unit cell having a shape of a closed figure that looks like a V or chevron may be formed at the (B) row which is a line of the linker portion.

When one end (a) of the pattern of the polymeric stent is connected to the other end (b) thereof, open figures at both ends of the (B) row may be connected to each other to form a closed figure. When one end (a) of the pattern of the polymeric stent is connected to the other end (b) thereof, open figures at both ends of the (B) row may be connected to each other to form a closed figure having a V or chevron shape, which is positioned in a direction opposite to the unit cell having a shape of a closed figure that looks like a V or chevron at the (A) row thereof.

In the repeating unit 300, the length of the linker portion 130 may be shorter than the distance between the bent portion of the first hinge portion 200 and the bent portion of the second hinge portion 250.

Accordingly, as depicted in FIG. 1, the unit cell having a shape of a closed figure that looks like a V or chevron at the (A) row may be larger than a closed figure having a V or chevron shape at the (B) row, which is formed by the linker portion. Further, in a longitudinal direction of the linker portion 130, the height of the unit cell having a shape of a closed figure that looks like a V or chevron at the (A) row may be larger than the height of a closed figure having a V or chevron shape at the (B) row, which is formed by the linker portion.

In the repeating unit 300, the length of the linker portion 130 may be longer than the distance between the bent portion of the first hinge portion 200 and the bent portion of the second hinge portion 250.

Accordingly, and as shown in FIG. 1, the unit cell having a shape of a closed figure that looks like a V or chevron at the (A) row may be smaller than a closed end having a V or chevron shape at the (B) row, which is formed by the linker portion. In addition, in a longitudinal direction of the linker portion 130, the height of the unit cell having a shape of a close figure shaped like a V or chevron at the (A) row may be smaller than the height of a closed figure having a V or chevron shape at the (B) row, which is formed by the linker portion.

Thus, as illustrated in FIGS. 1 and 2, a corner and an end of one repeating unit 300 are connected to a corner and an end of another unit cell. That is, in a polymeric stent as described herein, the repeating unit 300 does not have a corner or an end that is not connected to each other.

In some embodiments, the interior angle 400 of the second hinge portion may be about 100° or more. In some embodiments, the interior angle 400 of the second hinge portion may range from about 90° to about 160°, or more.

FIG. 4A illustrates a form of the unit cell when the interior angle 400 of the second hinge portion is about 90° and FIG. 4B illustrates a form of the unit cell when the interior angle 400 of the second hinge portion is about 160°.

FIG. 5A illustrates the pattern of the polymeric stent when the thickness of the unit cell 110 and the linker portion 130 is about 80 μm and FIG. 5B illustrates the pattern of the polymeric stent when the thickness of the unit cell 110 and the linker portion 130 is about 120 μm.

In a polymeric stent of the present disclosure, the length of the diameter, as the number of cells in a circumference and the thickness of the strut are modified, the interior angle of the second hinge portion, the area of the repeating unit, and the variations of the area ratio of the strut based on the area of the repeating unit are shown in the following Table 1.

TABLE 1

| | Number of cells | Thickness (um) | Diameter length (mm) | | | | |
|---|---|---|---|---|---|---|---|
| | | | 2 mm | 3 mm | 5 mm | 6 mm | 8 mm |
| Area of minimum unit cell (mm²) | 4 ea | 80 | 2.57 | 6.31 | 17.9 | 25.05 | 44.38 |
| | | 120 | 2.43 | 6.12 | 17.6 | 24.86 | 43.88 |
| | | 160 | 2.32 | 6.11 | 17.58 | 24.67 | 43.38 |
| | 9 ea | 80 | 0.45 | 1.15 | 3.39 | 4.74 | 8.52 |
| | | 120 | 0.39 | 1.06 | 3.22 | 4.77 | 8.29 |
| | | 160 | 0.36 | 1.07 | 3.32 | 4.74 | 8.07 |

TABLE 1-continued

| | Number of cells | Thickness (um) | Diameter length (mm) | | | | |
|---|---|---|---|---|---|---|---|
| | | | 2 mm | 3 mm | 5 mm | 6 mm | 8 mm |
| | 15 ea | 80 | 0.13 | 0.35 | 1.11 | 1.59 | 3.21 |
| | | 120 | — | 0.30 | 1.01 | 1.49 | 2.79 |
| | | 160 | — | — | 0.92 | 1.39 | 2.66 |
| Area ratio (%) | 4 ea | 80 | 17 | 10 | 6 | 5 | 4 |
| | | 120 | 26 | 16 | 10 | 8 | 6 |
| | | 160 | 35 | 21 | 12 | 12 | 8 |
| | 9 ea | 80 | 38 | 24 | 14 | 13 | 9 |
| | | 120 | 58 | 37 | 22 | 18 | 14 |
| | | 160 | 74 | 46 | 27 | 24 | 19 |
| | 15 ea | 80 | 65 | 43 | 25 | 21 | 13 |
| | | 120 | — | 64 | 38 | 32 | 24 |
| | | 160 | — | — | 52 | 43 | 32 |
| V strut length (mm) | 4 ea | 80 | 1.69 | 2.59 | 4.37 | 5.23 | 6.40 |
| | | 120 | 1.72 | 2.63 | 4.38 | 5.19 | 6.46 |
| | | 160 | 1.76 | 2.60 | 4.38 | 5.18 | 6.80 |
| | 9 ea | 80 | 0.79 | 1.18 | 1.94 | 2.32 | 2.94 |
| | | 120 | 0.85 | 1.16 | 1.95 | 2.31 | 2.84 |
| | | 160 | 0.91 | 1.16 | 1.92 | 2.30 | 3.01 |
| | 15 ea | 80 | 0.48 | 0.72 | 1015 | 1.3 | 1.74 |
| | | 120 | — | 0.71 | 1.19 | 1.34 | 1.83 |
| | | 160 | — | — | 1.05 | 1.42 | 1.86 |

When the diameter, the number of cells in a circumference and the thickness of the strut are modified, variations in the form of the unit cell are produced, examples of which are shown in the following Table 2.

TABLE 2

| Number of cells | Thickness (um) | Diameter length (mm) | | | | |
|---|---|---|---|---|---|---|
| | | 2 mm | 3 mm | 5 mm | 6 mm | 8 mm |
| 4 ea | 80 | ✧ | ✧ | ✧ | ✧ | ✧ |
| | 120 | | ✧ | ✧ | ✧ | ✧ |
| | 160 | | | ✧ | ✧ | ✧ |
| 9 ea | 80 | • | • | ✧ | ✧ | ✧ |
| | 120 | • | • | ✧ | ✧ | ✧ |
| | 160 | • | • | ✧ | ✧ | ✧ |
| 15 ea | 80 | . | . | . | ✧ | ✧ |
| | 120 | . | . | | ✧ | ✧ |
| | 160 | . | . | . | ✧ | ✧ |

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

A second harmonic generator was used to convert a laser having a wavelength of 1030 nm into a second harmonic generator laser output having a wavelength 515 nm and then used to form a V-shaped pattern on a polylactic acid tube.

The physical properties of the laser having a wavelength of 1030 nm can be as follows:
Spot Size=21.5 μm
Average Power=0.18 Watt
Repetition Rate=30 KHz
Speed=2.1 mm/sec Comparative Example 1

A process was performed in the same manner as in Example 1, except that a third harmonic generator was used to convert a laser having a wavelength of 1030 nm into a third harmonic generator laser having a wavelength 343 nm, which was then used to form a pattern on a polylactic acid tube.

Herein, the term "a third harmonic generator" refers to a device that divides the wavelength of the input laser by a factor of 3.

Comparative Example 2

A process was performed in the same manner as in Example 1, except that a pattern was formed on a polylactic acid tube with a laser having a wavelength of 1030 nm, but without using a second harmonic generator.

Experimental Example 1

SEM Observation

After forming a pattern with the laser in Example 1 and Comparative Examples 1 and 2, a surface exposed by cutting the polylactic acid tube was imaged captured by scanning electron microscope (SEM) and evaluated.

Figure 6:
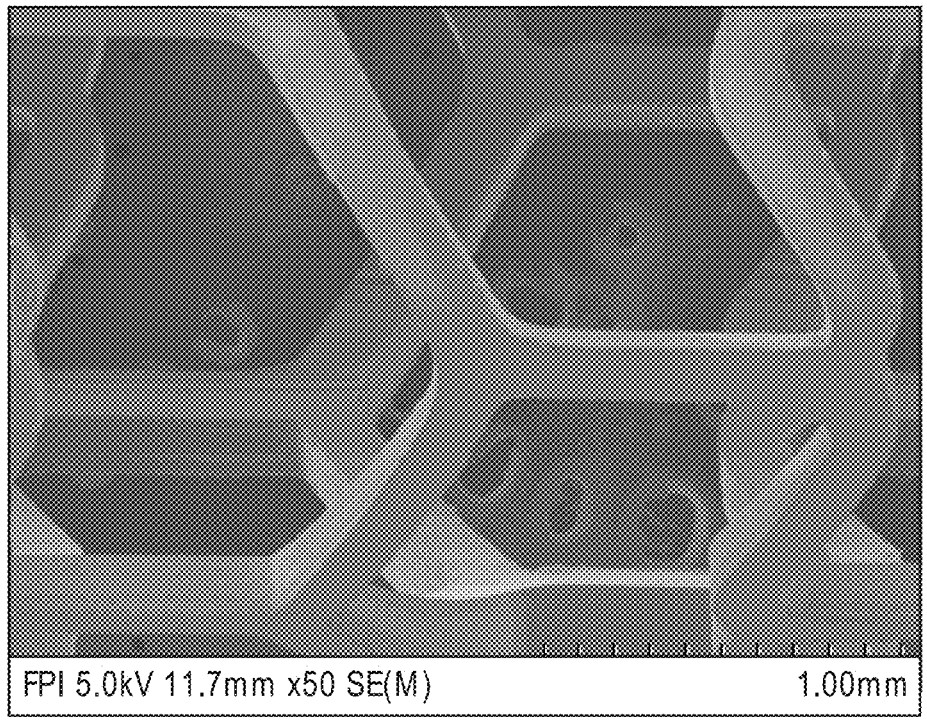
FIG. 6 is a scanning electron microscope (SEM) photograph of an embodiment of a polymeric stent in which a pattern of Example 1 is formed.
Figure 7:
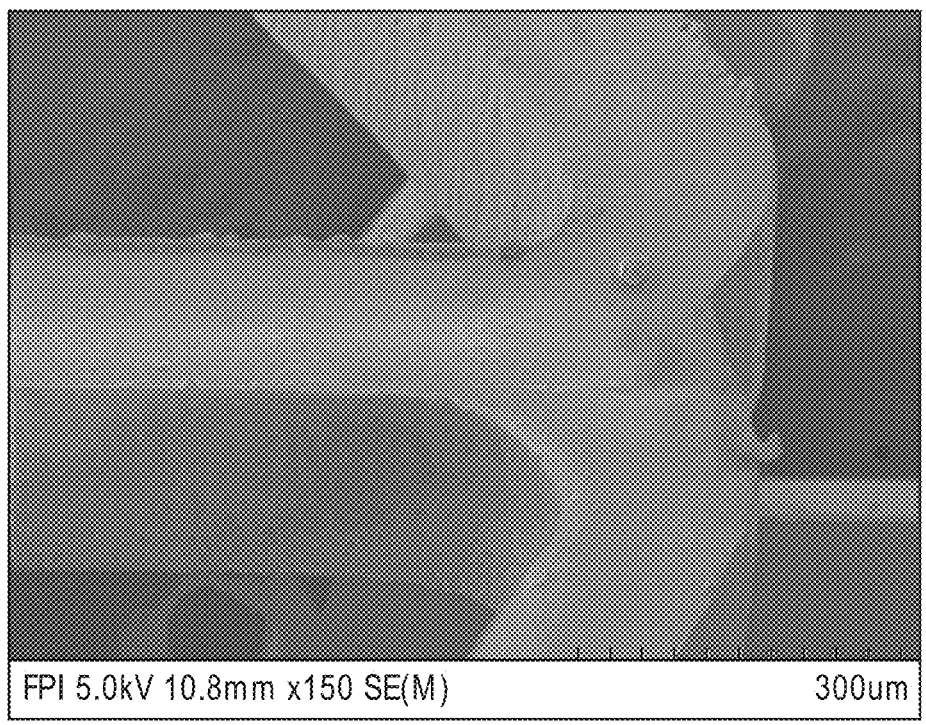
FIGS. 7 and 8 are SEM photographs taken of a cut surface of embodiments of a polymeric stent in which the pattern of Example 1 is formed.
Figure 8:
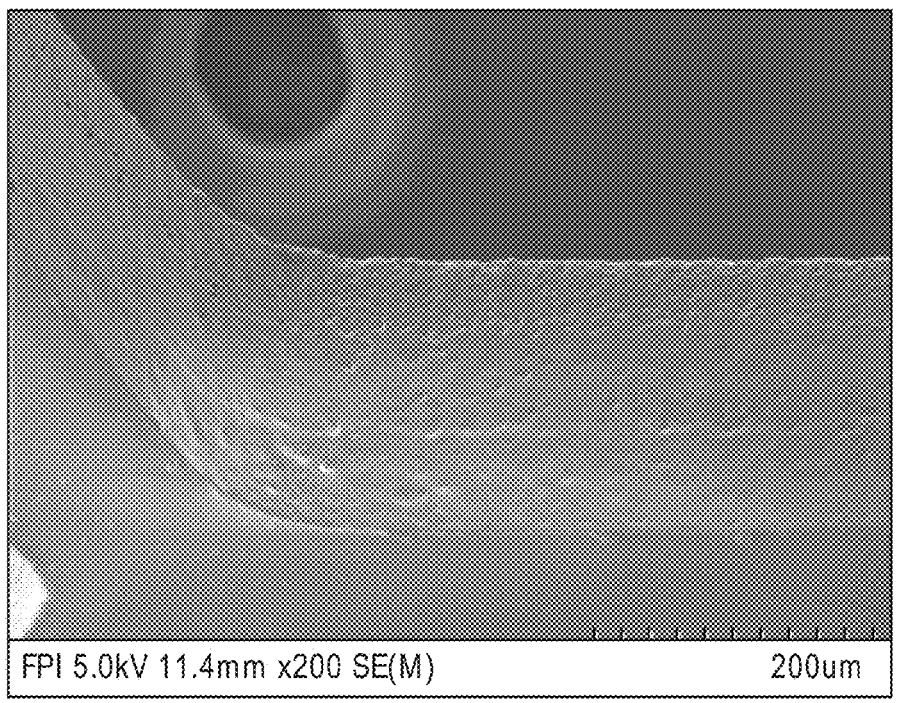

Photographs of exemplary cut surfaces produce by the method of Example 1 are illustrated in FIGS. 6 to 8.

FIG. 6 is a SEM photograph of a polymeric stent produced by the method of Example 1. The image depicts one side surface of a polymeric stent on which a pattern was formed.

FIG. 7 is a SEM photograph of a polymeric stent produced by the method of Example 1. The image shows a connecting part of struts in a polymeric stent on which a V-shaped pattern was formed. It can be seen that the cut surface of the strut, and the surrounding portions, were cleanly cut.

FIG. 8 is a SEM photograph of a polymeric stent produced by way of the method of Example 1. The image shows a cut surface of a polymeric stent on which a V-shaped pattern was formed. The evidence indicates that the polymeric stent was cut without causing damages that would have been caused if there had been overheating of the polymeric material.

Figure 9:
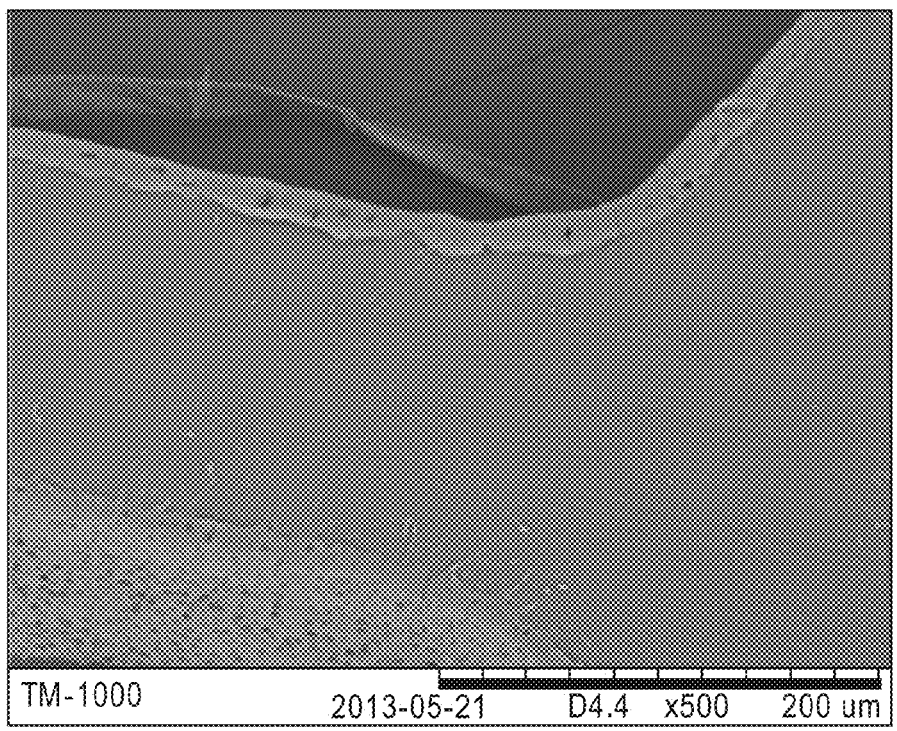
FIGS. 9 and 10 are SEM photographs taken of a cut surface of embodiments of a polymeric stent in which a pattern of Comparative Example 1 is formed.
Figure 10:
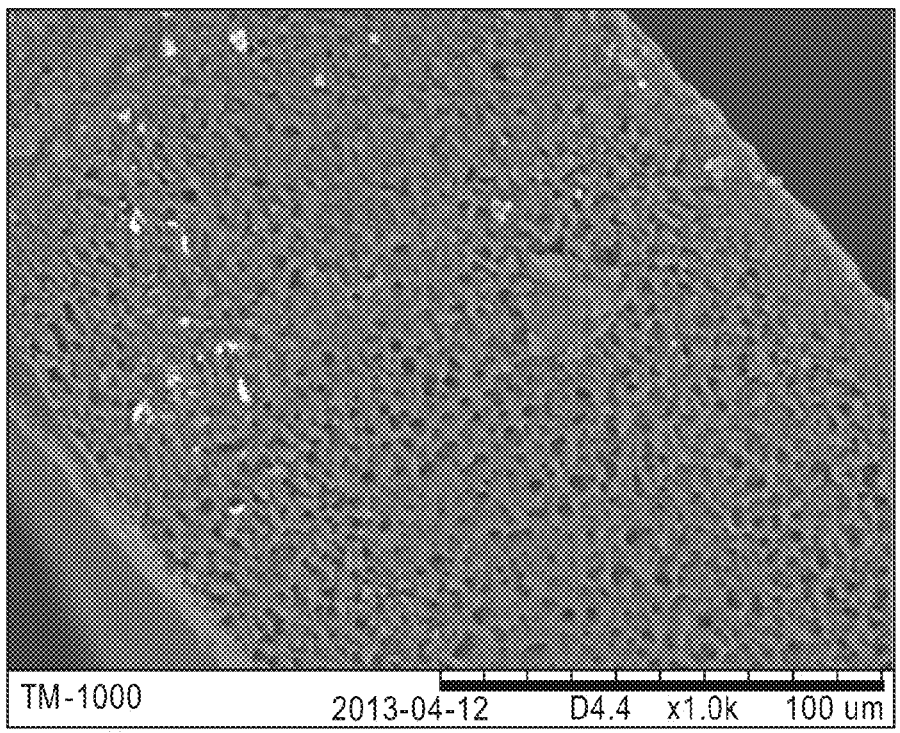

A photograph taken of the cut surface of Comparative Example 1 is illustrated in FIGS. 9 and 10. FIG. 9 is a SEM photograph of a polymeric stent produced by a method of Comparative Example 1. The image shows a connecting part of struts in a polymeric stent on which a V-shaped pattern was formed. It can be seen that the surrounding portions of the cut surface of the strut were polymer-modified. FIG. 10 is a SEM photograph of a stent produced by the method of Comparative Example 1. The image shows a cut surface of a polymeric stent on which a V-shaped pattern was formed, and it can be seen that the cut surface was relatively cleanly cut.

Figure 11:
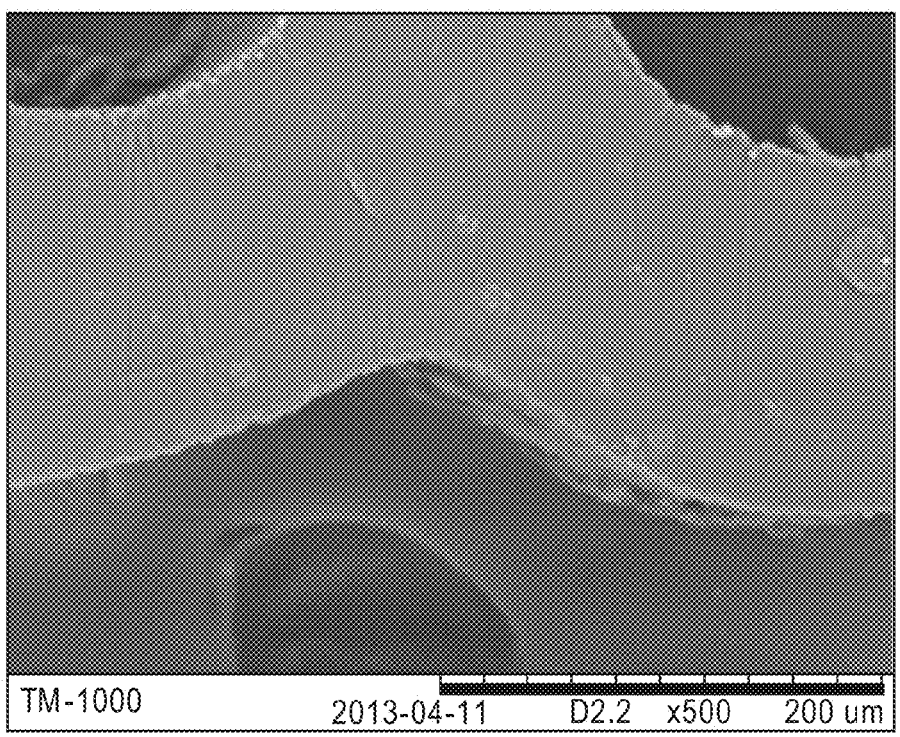
FIG. 11 is a SEM photograph taken of a cut surface of an embodiment of a polymeric stent in which a pattern of Comparative Example 2 is formed.

A photograph taken of the cut surface of a stent produced by the method of Comparative Example 2 is illustrated in FIG. 11. FIG. 11 is a SEM photograph of a polymeric stent produced by the method of Comparative Example 2. It can be seen that the cut surface of the polymeric stent on which the V-shaped pattern was formed was not clean and there is evidence of heat-induced damage at the cut surface.

Experimental Example 2

Gel permeation chromatography (GPC) was used to measure the number average molecular weight (Mn) and the polydispersity index (PDI, Mw/Mn) of a polylactic acid (PLA) tube before the laser processing, and of a polylactic acid stent after laser processing methods described in Example 1, Comparative Example 1 and Comparative Example 2 respectively. The variation in polydispersity index (PDI) represented by the following Equation 1, and the variation in average molecular weight represented by the following Equation 2 were calculated.

$$\text{Variation in Polydisperity Index}(\%) = \frac{B - A}{A} \times 100 \quad \text{Equation 1}$$

In Equation 1,
A is a polydispersity index of a polylactic acid (PLA) tube before a pattern is formed on the polylactic acid tube, and
B is a polydispersity index of the polylactic acid (PLA) polymeric stent after the pattern is formed on the polylactic acid tube.

$$\text{Variation in Average Molecular Weight}(\%) = \frac{C - D}{C} \times 100 \quad \text{Equation 2}$$

In Equation 2,
C is an average molecular weight of a polylactic acid tube before a pattern is formed, and
D is an average molecular weight of the polymeric stent after the pattern is formed.

In this case, an HFIP gel column (Agilent) was used as a column in the measurement of GPC. A solution of 10 mM sodium trifluoroacetate dissolved in hexafluoroisopropanol (HFIP) was used as the eluent. Transport speed was 0.2 ml/min.

The results measured by GPC are shown in the following Table 3.

TABLE 3

|  | Example 1 | | Comparative Example 1 | | Comparative Example 2 | |
| --- | --- | --- | --- | --- | --- | --- |
|  | Mn (KDa) | Mw/Mn | Mn (KDa) | Mw/Mn | Mn (KDa) | Mw/Mn |
| PLA tube expanded before laser processing | 222 | 1.5 | 167 | 1.9 | 167 | 1.9 |
| PLA stent processed with laser | 195 | 1.6 | 28 | 4.6 | 129 | 2.3 |
| Variation in PDI | 6.67% | | 142.11% | | 21.05% | |
| Variation in Mn | 12.16% | | 83.23% | | 22.75% | |

As shown in Table 3, in Example 1, there was almost no change in variation in the molecular weight after laser processing. In contrast, in Comparative Example 1, molecular weight was rapidly decreased after laser processing was used to form the stent pattern. The polydispersity index was also significantly increased.

As the C═O bond of polylactic acid absorbs energy at wavelengths of 280 nm and 190 nm, and the C—C bond and the C—H bond of polylactic acid absorbs energy at a wavelength shorter than 180 nm, when processing was performed with a femtosecond laser at the wavelength ranges shorter than the ultraviolet rays or the ultraviolet rays, these wavelengths were absorbed and the polylactic acid in the stent was photo-degraded. Accordingly, the femtosecond laser having the wavelength ranges in the UV or short than UV range are not appropriate for processing the polylactic acid stent.

Further, in Comparative Example 2, it can be seen that a variation in polydispersity index was significant. The results showed that the distribution of molecular weights was broadened.

It should also be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method for manufacturing a polymeric stent, comprising:

forming a pattern on a polymer tube with a laser;
    wherein the pattern formed on the polymer tube comprises a plurality of repeating units comprising a plurality of unit cells, wherein each unit cell has a V-shaped configuration and comprises a first hinge portion having a first end and a second end, wherein the first hinge portion is bent inwardly to the unit cell and a second hinge portion having a first end and a second end, wherein the second hinge portion is facing the first hinge portion and bent outwardly from the unit cell; and a linker portion extended outwardly from a bent portion of the second hinge portion;
    wherein the repeating units are disposed such that an end of a linker portion of one repeating unit is connected to a bent portion of a first hinge portion of an adjacent repeating unit, or
    the first end of a first hinge portion and the first end of a second hinge portion of one repeating unit are connected to an end of a first hinge portion and an end of a second hinge portion of the adjacent repeating unit, respectively;
    wherein the plurality of repeating units is manufactured from a biodegradable polymer;
    wherein the thickness of the unit cell and the strut of the linker portion is 80 to 120 μm;
    wherein a polydispersity index of the polymeric stent ranges from 1 to 2;
    wherein the pattern is formed on the polymer tube using a laser having a pulse width of 1 fs to 900 fs and a repetition rate of 2 kHz to 200 kHz;
    wherein the laser is a second harmonic generator laser in which a wavelength ranging from 940 nm to 1552 nm is converted; and
    wherein the polymeric stent has a target diameter and is capable of withstanding expansion of up to 1 mm beyond the target diameter without forming fractures or cracks.

2. The method of claim 1, wherein the second harmonic generator laser is a laser in which a wavelength ranging from 1000 nm to 1100 nm is converted.

3. The method of claim 1, wherein the polymer tube is made of polylactic acid.

4. The method of claim 1, wherein an output wavelength of the second harmonic generator laser ranges from 470 nm to 776 nm.

5. The method of claim 1, wherein an output wavelength of the second harmonic generator laser ranges from 500 nm to 550 nm.

6. The method of claim 3, wherein a variation in polydispersity index (PDI) of the polymeric stent represented by the following Equation 1 is 20% or less:

$$\text{Variation in Polydisperity Index}(\%) = \frac{B - A}{A} \times 100. \quad \text{(Equation 1)}$$

wherein, in Equation 1:
A is a polydispersity index of a polylactic acid tube before a pattern is formed; and
B is a polydispersity index of the polymeric stent after the pattern is formed.

7. The method of claim 3, wherein a variation in average molecular weight of the polymeric stent represented by the following Equation 2 is 20% or less:

$$\text{Variation in Average Molecular Weight}(\%) = \frac{C - D}{C} \times 100\%  \quad \text{(Equation 2)}$$

wherein, in Equation 2:
C is an average molecular weight of a polylactic acid tube before a pattern is formed; and
D is an average molecular weight of the polymeric stent after the pattern is formed.

8. The method of claim 1, further comprising:
    applying to the polymeric stent a composition effective to prevent restenosis of a lumen in a body vessel; and
    radially compressing the polymeric stent.

9. The method of claim 1, further comprising:
    forming a groove or a hole on at least one of the struts of the linker portion; and
    affixing a radiomarker to the groove or the hole.

* * * * *